United States Patent
Basu et al.

(10) Patent No.: US 8,027,427 B2
(45) Date of Patent: Sep. 27, 2011

(54) SYSTEMS AND METHOD FOR SCANNING A CONTINUOUS STREAM OF OBJECTS

(75) Inventors: Samit Kumar Basu, Fremont, CA (US); Eugene Alex Ingerman, San Francisco, CA (US)

(73) Assignee: Morpho Detection, Inc., Newark, CA (US)

( * ) Notice: Subject to any disclaimer, the term of this patent is extended or adjusted under 35 U.S.C. 154(b) by 121 days.

(21) Appl. No.: 12/550,597

(22) Filed: Aug. 31, 2009

(65) Prior Publication Data

US 2011/0051886 A1   Mar. 3, 2011

(51) Int. Cl.
   *H05G 1/60* (2006.01)
(52) U.S. Cl. .............. 378/8; 378/20; 378/95; 382/131; 382/132
(58) Field of Classification Search .............. 378/4, 8, 378/15, 16, 19, 20, 57, 95, 114, 901; 382/131, 382/132
   See application file for complete search history.

(56) References Cited

U.S. PATENT DOCUMENTS

| 5,661,774 | A | 8/1997 | Gordon et al. |
| 7,327,853 | B2 | 2/2008 | Ying et al. |
| 7,720,523 | B2 * | 5/2010 | Omernick et al. ............ 600/427 |
| 2008/0192886 | A1 | 8/2008 | Pack |
| 2009/0003514 | A1 | 1/2009 | Edic et al. |
| 2009/0003515 | A1 | 1/2009 | Naidu et al. |

OTHER PUBLICATIONS

U.S. Appl. No. 12/401,907, filed Mar. 11, 2009.
U.S. Appl. No. 12/391,470, filed Feb. 24, 2009.

* cited by examiner

*Primary Examiner* — Jurie Yun
(74) *Attorney, Agent, or Firm* — Armstrong Teasdale LLP

(57) ABSTRACT

A method for scanning a stream of objects includes continuously acquiring raw data of the stream of objects using an X-ray system, that includes a detector. The raw data of the stream of objects is rebinned into at least one two-dimensional sinogram. A leading edge and a trailing edge of a first object of the stream of objects is determined from the at least one two-dimensional sinogram and a three-dimensional image of the first object is reconstructed using the at least one two-dimensional sinogram.

20 Claims, 3 Drawing Sheets

SYSTEMS AND METHOD FOR SCANNING A CONTINUOUS STREAM OF OBJECTS

BACKGROUND OF THE INVENTION

1. Field of the Invention

The embodiments described herein relate generally to tomographic systems, such as computed tomography (CT) systems, and, more particularly, to CT systems that scan a continuous stream of objects, such as luggage, for explosive or contraband detection.

2. Description of the Related Art

At least some known explosive detection systems use tomographic systems to scan a continuous stream of objects. In such tomographic systems, it is generally necessary to partition data generated by the tomographic system into blocks associated with each object in the stream of objects. For such tomographic systems to perform partitioning of the data successfully, the tomographic system determines an extent of each object and completes data acquisition for each object as each object passes through the tomographic system. As used herein, the term "extent of an object" refers to the physical boundaries, dimensions, and/or measurements of the object, such as the physical volume of the object, and/or data representing the physical object. In at least one known explosive detection system, a machine control for a scanning device generally receives information, such as an identification tag, about each object from an external system that transports the objects into a scanning device, such as a CT system. At least one CT system includes passive curtains to shield an external environment from X-ray radiation produced by the CT system. However, objects passing through the passive curtains may be repositioned, such as by moving adjacent each other or shifting orientation, before and/or inside the scanning device. Such repositioning may cause confusion between the extent of an object as externally measured, and the extent and position of the object once inside the scanning device. As such, there is a need to determine extents of objects within the scanning device.

In at least some known tomographic systems for scanning a stream of objects, the acquisition system, which captures scan data of an examination area, identifies a leading edge and a trailing edge of an object using an internal light sensor array. However, such a light sensor array may provide a rapid determination of a leading edge and a trailing edge of an object, but may lack accuracy and may fail to properly determine a leading edge and a trailing edge of irregularly shaped objects. As such, there is a need to quickly and accurately determine the physical extents of objects.

BRIEF SUMMARY OF THE INVENTION

In one aspect, a method for scanning a stream of objects is provided. The method includes continuously acquiring raw data of the stream of objects using an X-ray system including a detector, rebinning the raw data of the stream of objects into at least one two-dimensional sinogram, determining a leading edge and a trailing edge of a first object of the stream of objects from the at least one two-dimensional sinogram, and reconstructing a three-dimensional image of the first object using the at least one two-dimensional sinogram.

In another aspect, a scanning system is provided. The scanning system includes a conveyor configured to transport a stream of objects through the scanning system, and a computed tomography (CT) system configured to generate an image of a first object of the stream of objects. The CT system includes a detector and a control system. The control system is configured to continuously acquire raw data of the stream of objects from the detector, rebin the raw data of the stream of objects into at least one two-dimensional sinogram, determine a leading edge and a trailing edge of the first object from the at least one two-dimensional sinogram, and reconstruct a three-dimensional image of the first object using the at least one two-dimensional sinogram.

In yet another aspect, a computed tomography (CT) system is provided. The CT system includes a radiation source, a detector configured to detect radiation emitted from the radiation source, and a control system that includes an object detection subsystem and an acquisition subsystem configured to continuously acquire raw data of a stream of objects from the detector. The object detection subsystem is configured to rebin the raw data of the stream of objects into at least one two-dimensional sinogram and determine a leading edge and a trailing edge of a first object of the stream of objects) from the at least one two-dimensional sinogram. The control system also includes a reconstruction subsystem configured to reconstruct an image of the first object using the at least one two-dimensional sinogram.

The embodiments described herein use a CT system to determine a leading edge and a trailing edge of each object in a stream of objects being scanned by the CT system. The CT system continuously scans the stream of objects within a CT plane, and generates at least one two-dimensional sinogram by rebinning the projection data. Once the leading edge of an object is determined from processing the sinogram data, the CT system begins processing the sinogram data further to obtain a three-dimensional volume reconstruction. Once the trailing edge of an object is determined from processing the sinogram data, the CT system completes the three-dimensional volume reconstruction and sends the data for further processing steps (e.g. automated inspection, display on computer screen, saving to storage disk). The CT system only reconstructs three-dimensional volume data when leading and trailing edges of objects are determined. Accordingly, edges and/or boundaries of objects within the CT system are determined, and images are reconstructed when an object is in the CT plane and not when an object is not present in the CT plane, such as when a gap in the stream of objects is within the CT plane.

BRIEF DESCRIPTION OF THE DRAWINGS

FIG. 1 is a schematic view of an exemplary scanning system.

FIG. 2 is a schematic view of an exemplary computed tomography (CT) system that may be used with the scanning system shown in FIG. 1.

FIG. 3 is a flowchart of an exemplary method that may be performed using the scanning system shown in FIG. 1.

DETAILED DESCRIPTION OF THE INVENTION

The embodiments described herein detect a leading edge (LE) and a trailing edge (TE) of each object of a stream of objects through a computed tomography (CT) system to determine when to reconstruct an image of one or more objects. As such, a data stream is partitioned to correspond to each object that passes through the CT system. In the embodiments described herein, the CT system preprocesses signals measured on a detector within the CT system to determine the LE and/or the TE. In one embodiment, a control system continuously monitors detector data received by the control system. When an object enters into a CT plane, the object creates a signature signal change on the detector. For example, absorption of X-rays by the object will result in a decrease in a number of photons detected by the detector. The control system monitors the detector data and continuously rebins the detector data into two-dimensional (2D) sinograms. Each 2D sinogram represents a 2D "slice" of the object.

The control system continuously calculates a total mass of each 2D slice by computing the sum of all the values in the 2D sinogram. This sum is equal to the total mass of each 2D slice as a consequence of the Fourier Slice Theorem. The control system compares the total mass in each 2D slice to a threshold value. When the control system determines that a 2D slice exceeds the threshold value, the control system marks the current 2D slice as indicative of the LE of the object. When the control system determines that the total mass in a subsequent 2D slice falls below the threshold value, the control system marks the 2D slice as indicative of the TE of the object and terminates recording and/or reconstructing an image of the received data. Data continues to be acquired and received by the control system, however, such data is not recorded and/or reconstructed. A delay can be used to continue marking 2D slices after the detection of the TE as part of the object, if necessary.

As used herein, the phrase "reconstructing an image" is not intended to exclude embodiments in which data representing an image is generated but a viewable image is not. Therefore, as used herein the term "image" broadly refers to both viewable images and data representing a viewable image. However, many embodiments generate (or are configured to generate) at least one viewable image. Additionally, although described in detail in a CT inspection setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), X-ray Tomo-synthesis, and in both non-medical settings and medical settings.

Figure 1:
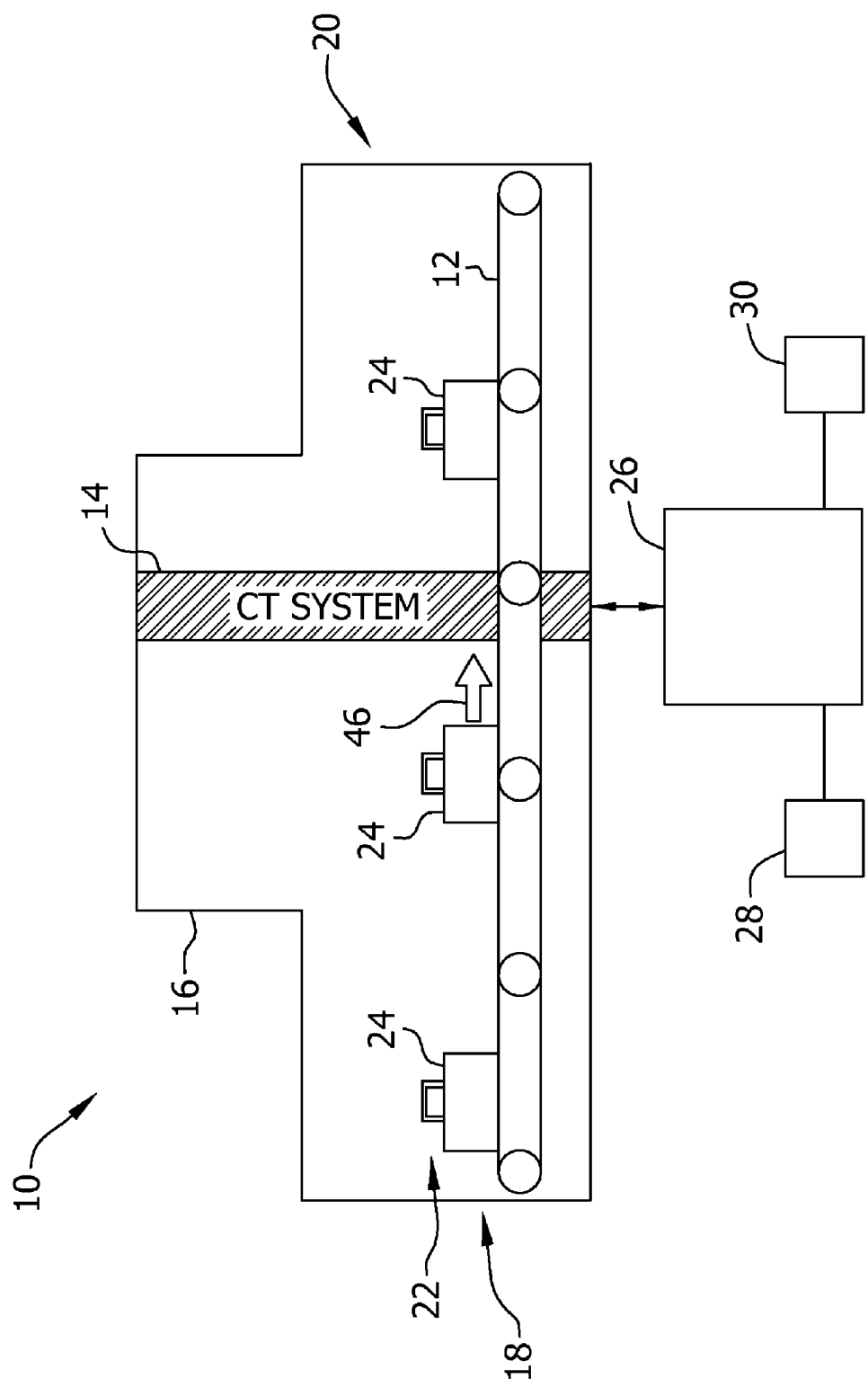
FIGS. 1-3 show exemplary embodiments of the systems and method described herein.

FIG. 1 is a schematic view of an exemplary scanning system 10. Scanning system 10 includes a conveyor 12 and a CT system 14 positioned at least partially within a housing 16. Conveyor 12 extends between an inlet 18 of housing 16 and an outlet 20 of housing 16. Further, conveyor 12 is configured to transport a stream 22 of objects 24 through scanning system 10. In the exemplary embodiment, stream 22 includes at least one object 24. Conveyor 12 extends through CT system 14 and conveys objects 24 sequentially through CT system 14 such that each object 24 is scanned by CT system 14. CT system 14 is configured to scan objects 24 one at a time in the exemplary embodiment.

A control system 26 is in operational control communication with conveyor 12 and CT system 14. As used herein, "operational control communication" refers to a link, such as a conductor, a wire, and/or a data link, between two or more components of scanning system 10 that enables signals, electric currents, and/or commands to be communicated between the two or more components. The link is configured to enable one component to control an operation of another component of scanning system 10 using the communicated signals, electric currents, and/or commands. Further, as used herein, the term "control system" is not limited to integrated circuits referred to in the art as a control system, but broadly refers to a computer, microcontroller, a microcomputer, a programmable logic controller, an application specific integrated circuit, and/or any other programmable circuit.

Control system 26 includes a central processing unit and may include a device, such as a floppy disk drive or a compact-disc read-only memory (CD-ROM) drive, for reading data from a computer-readable medium, such as a floppy disk, a compact disc-read only memory (CD-ROM), a magneto-optical disk (MOD), and/or a digital versatile disc (DVD). In an alternative embodiment, control system 26 executes instructions stored in firmware. In the exemplary embodiment, control system 26 controls speed, acceleration, deceleration, starting, stopping, and/or any suitable function of conveyor 12. Moreover, control system 26 controls CT system 14 and/or conveyor 12 to acquire data relating to objects 24, as described in more detail below. In the exemplary embodiment, control system 26 is also in communication with an input device 28 and a display device 30. Display device 30 may include, without limitation, a liquid crystal display (LCD), a cathode ray tube (CRT), and/or any suitable output device. Input device 28 includes, without limitation, a mouse and a keyboard.

Figure 2:
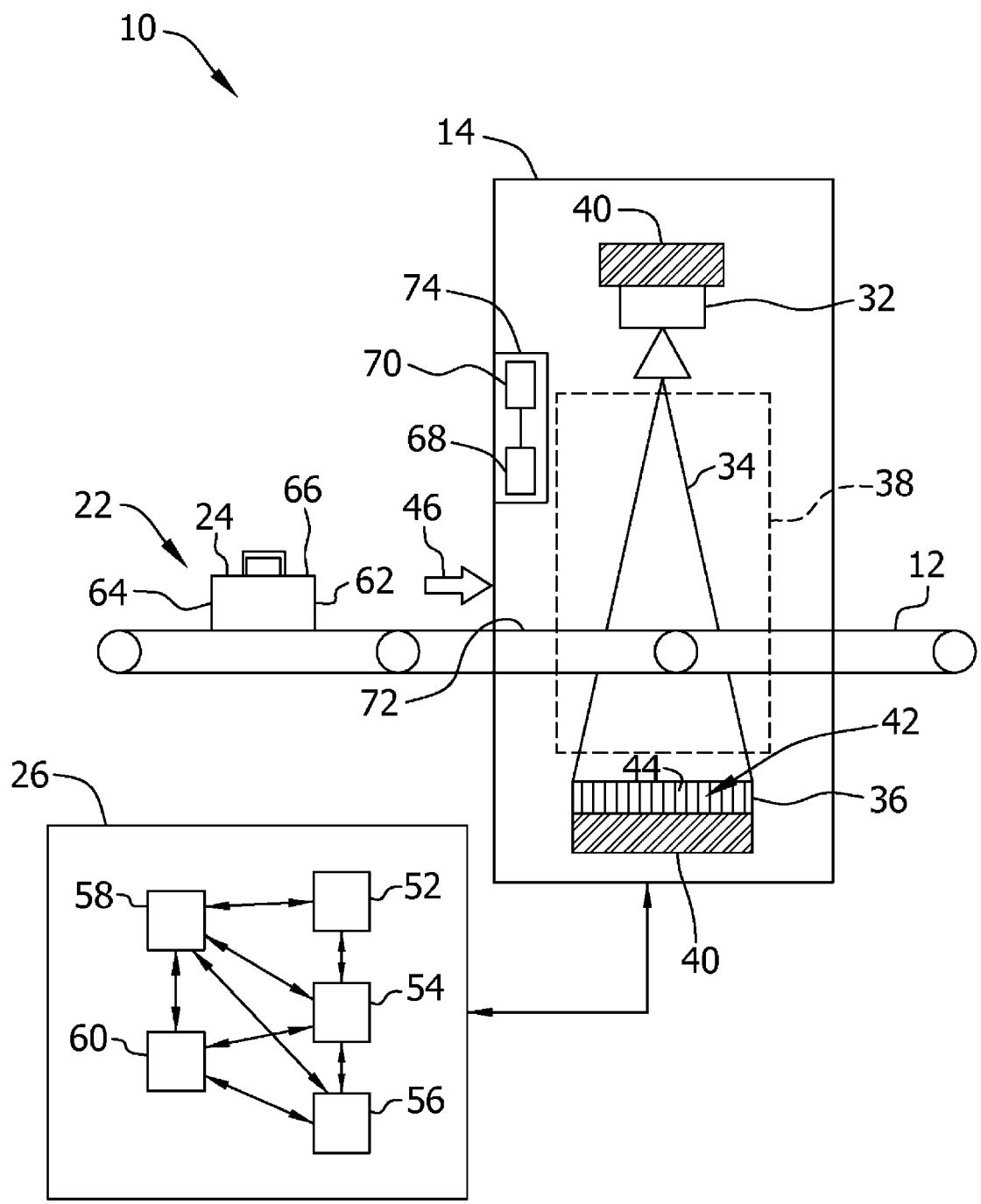

FIG. 2 is a schematic view of exemplary CT system 14 that may be used with scanning system 10 (shown in FIG. 1). CT system 14 includes a radiation source 32 for emitting radiation 34 and a detector 36 for detecting emitted radiation 34. A CT plane 38 is defined between radiation source 32 and detector 36. In the exemplary embodiment, radiation source 32 and detector 36 are coupled to a gantry 40 for rotation about CT plane 38. Alternatively, radiation source 32 and/or detector 36 are coupled within CT system 14 such that radiation source 32 and/or detector 36 are stationary with respect to CT plane 38. In the exemplary embodiment, CT system 14 performs a continuous helical scan as stream 22 of objects 24 passes through CT plane 38. As used herein, CT plane 38 is not limited to a strictly planar region, but may also encompass, for example, a conical region, a fan-shaped region, or any suitable region that enables CT system 14 to operate as described herein.

In the exemplary embodiment, control system 26 is in operational control communication with radiation source 32 and detector 36. Control system 26 controls emission of radiation 34 from radiation source 32 and receives data from detector 36 as described in more detail herein. Further, control system 26 controls components of CT system 14 in any suitable manner that enables CT system 14 to function as described herein. In the exemplary embodiment, radiation source 32 emits radiation 34 as X-rays in a cone-beam. Alternatively, radiation source 32 may emit any suitable radiation having any suitable beam shape, such as a fan beam.

Detector 36 includes a plurality of rows 42 and columns (not shown) of detector elements 44. Each row 42 extends in a direction that is substantially perpendicular to a direction of object travel indicated by directional arrow 46. The columns are substantially parallel to the object travel direction indicated by directional arrow 46. Each detector element 44 produces an electrical signal that represents an intensity of an impinging radiation beam and, hence, the attenuation of the beam as the beam passes through object 24. The electrical signals produced by detector elements 44 are transmitted to control system 26.

In the exemplary embodiment, control system 26 includes an object detection subsystem 52, an acquisition subsystem 54, and a reconstruction subsystem 56. Control system 26 also includes a memory 58 for data storage and a buffer 60 for temporary data storage. Although memory 58 and buffer 60 are shown as separate components, it should be understood that memory 58 and buffer 60 may be the same component within control system 26. Memory 58 and/or buffer 60 may be a random access memory (RAM) and/or a read only memory (ROM).

In the exemplary embodiment, object detection subsystem 52 is configured to determine a leading edge 62 and a trailing edge 64 of a first object 66 in stream 22 using radiation detected by detector 36, as described in more detail herein. Acquisition subsystem 54 is configured to process and/or record raw data of first object 66 based on the determination of leading edge 62 and trailing edge 64. Reconstruction subsystem 56 is configured to reconstruct an image of first object 66 using at least the processed and/or recorded raw data, as described in more detail herein.

In the exemplary embodiment, CT system 14 includes a backup detector 74 that monitors an entrance to CT plane 38. In the exemplary embodiment, backup detector 74 includes a motion detector 70 that is operatively coupled to at least one light sensor 68. Light sensor 68 and motion detector 70 are positioned upstream of gantry 40 with respect to the direction of object travel as indicated by directional arrow 46. Motion detector 70 is configured to determine a presence of an object 24 entering CT plane 38. In the exemplary embodiment, light sensor 68 includes an infrared sensor. In one embodiment, light sensor 68 is a vertical sensor array, or light curtain, that includes a plurality of infrared transmitters and an opposing plurality of infrared receivers, and is oriented in a first plane, such as a vertical plane or an approximately vertical plane. The first plane is perpendicular to a plane defined by a surface 72 of conveyor 12. In an alternative embodiment, light sensor 68 is a point sensor that projects an infrared beam that is oriented in a second plane perpendicular to the first plane. As such, the second plane is a horizontal plane, or an approximately horizontal plane, that is approximately parallel to surface 72. Light sensor 68 projects an infrared beam across surface 72 such that, when object 24 obstructs the infrared beam, thereby preventing the infrared beam from being received by a receiver positioned opposite light sensor 68, object 24 is registered by light sensor 68 as having crossed a particular marker point.

In the exemplary embodiment, motion detector 70 is communicatively coupled to control system 26. Motion detector 70 monitors light sensor 68 to detect when object 24 has crossed the marker point. Motion detector 70 notifies control system 26 that object 24 is entering CT plane 38. If one or more components of control system 26 and/or CT system 14 is de-energized or is in a low power state when motion detector 70 notifies control system 26 that object 24 is entering CT plane 38, the one or more components of control system 26 and/or CT system 14 is energized to a full power state and resumes operation as described herein.

Figure 3:
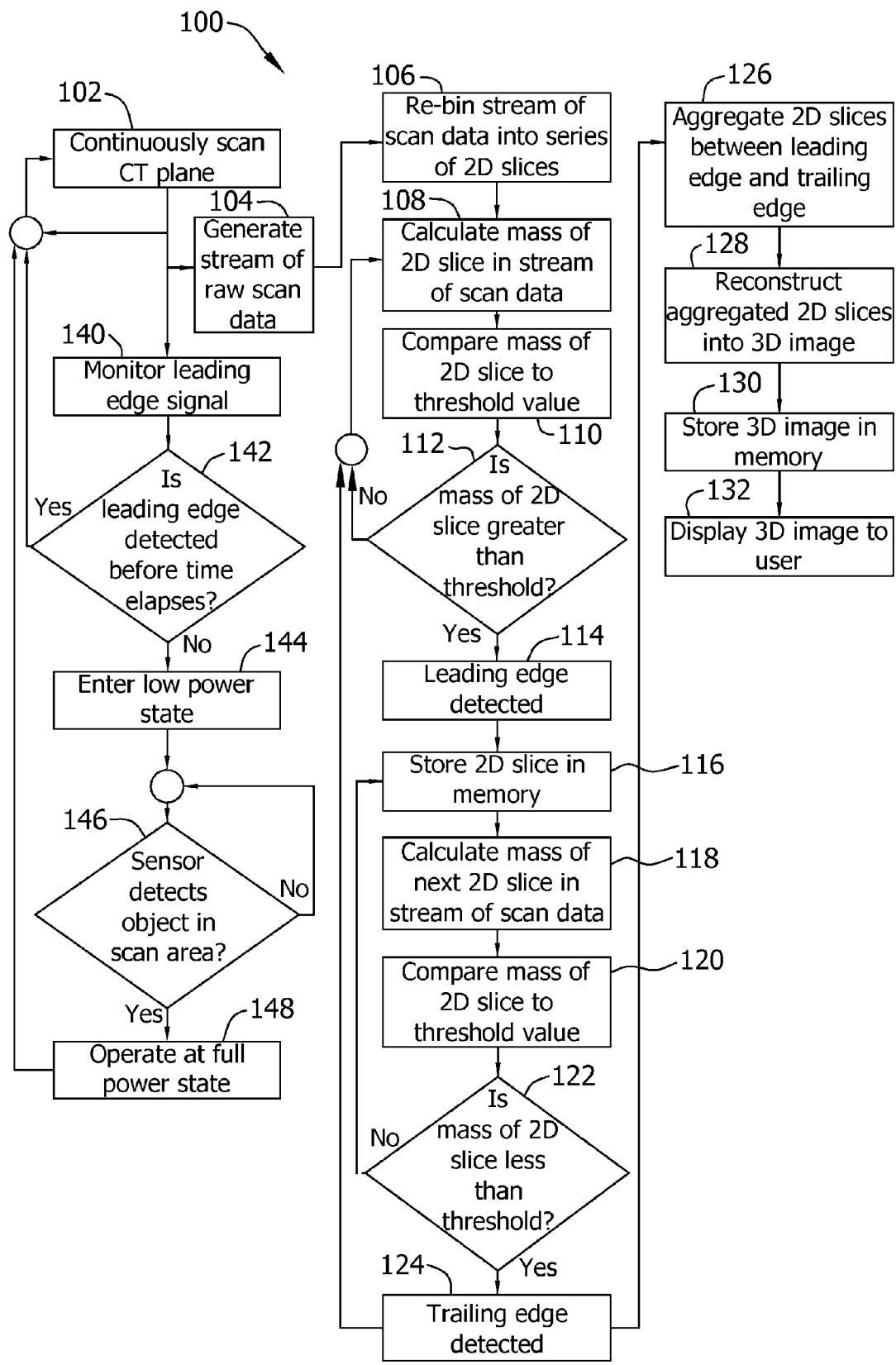

FIG. 3 is a flowchart of an exemplary method 100 for scanning a stream of objects that may be performed using scanning system 10 (shown in FIG. 1) and CT system 14 (shown in FIG. 2). In the exemplary embodiment, method 100 is used to scan stream 22 of objects 24 (shown in FIG. 1) with CT system 14. In the exemplary embodiment, method 100 is at least partially performed or controlled by control system 26 (shown in FIG. 2).

Method 100 includes continuously scanning 102 CT plane 38 (shown in FIG. 2) using acquisition subsystem 54 (shown in FIG. 2) of CT system 14. More specifically, radiation source 32 emits radiation 34 (both shown in FIG. 2), such as X-rays, towards CT plane 38 as gantry 40 (shown in FIG. 2) continuously rotates about CT plane 38 and conveyor 12 (shown in FIG. 2). Detector 36 (shown in FIG. 2) measures an amount of radiation 34 received from radiation source 32 and generates 104 a stream of raw scan data. More specifically, an energy level of radiation 34 emitted from radiation source 32 is attenuated by an amount based on the characteristics of object 24 within CT plane 38. Each detector element 44 measures an amount of energy received from the attenuated radiation 34 that has passed through CT plane 38. Detector 36 aggregates data from each detector element 44 and transmits the data in a data stream, such as one or more electrical signals, to object detection subsystem 52 (shown in FIG. 2).

Object detection subsystem 52 continuously receives the generated 104 stream of raw scan data and rebins 106 the raw scan data into a plurality of substantially two-dimensional (2D) planar representations (sinograms or slices) of the raw scan data. In the rebinning step, for every 2D slice, a set of detector values that are most consistent with the slice are selected and interpolated to the 2D slice. In the exemplary embodiment, a Ray Consistency Based Reconstruction algorithm described in U.S. Patent Application Publication Number 2008/0192886 is used. Alternatively, any other multi-slice type algorithm may be used, such as advanced single-slice rebinning (ASSR). More specifically, the stream of raw scan data is continuously rebinned 106 into successive 2D sinograms or slices, and object detection subsystem 52 stores each 2D slice in buffer 60 (shown in FIG. 2). In the exemplary embodiment, object detection subsystem 52 uses the data contained in the 2D slice to calculate 108 a total mass of matter within the 2D slice. Alternatively, object detection subsystem 52 uses the data contained in the 2D slice to calculate 108 an average density of matter within the 2D slice. In the exemplary embodiment, after the raw scan data has been rebinned 106 into 2D slices, the raw scan data is discarded. In an alternative embodiment, the raw scan data is stored in buffer 60 and/or memory 58 of control system 26 after the raw scan data has been rebinned 106. As used herein, the terms "2D sinogram" and "2D slice" are interchangeable.

Object detection subsystem 52 compares 110 the calculated 108 total mass of the 2D slice with a threshold value. In the exemplary embodiment, the threshold value is a predetermined threshold value. The threshold value may be changed as needed, by, for example, using input device 28 (shown in FIG. 1) to enter a new threshold value into control system 26. If object detection subsystem 52 determines 112 that the total mass of the 2D slice is greater than the threshold value, then object detection subsystem 52 determines that a leading edge 62 of an object 24 has been detected 114. If the total mass of the 2D slice is less than or equal to the threshold value, object detection subsystem 52 calculates 108 the total mass of the next 2D slice and compares 110 the total mass of the 2D slice to the threshold as described above. In one embodiment, if the total mass of the 2D slice is less than or equal to the threshold value, the 2D slice is discarded and/or overwritten in buffer 60.

If leading edge 62 of object 24 has been detected 114, the 2D slice is stored 116 in memory 58. After leading edge 62 is detected 114, object detection subsystem 52 calculates 118 a total mass in the next 2D slice in the same manner as calculated 108 above. Object detection subsystem 52 compares 120 the total mass of the 2D slice to the threshold value as described above. If object detection subsystem 52 determines 122 that the total mass in the 2D slice is less than the threshold value, then object detection subsystem 52 determines that a trailing edge 64 of object 24 has been detected 124. If the total mass of the 2D slice is greater than or equal to the threshold value, then object detection subsystem 52 determines that no trailing edge 64 of object 24 has been detected. In such case, the 2D slice is stored 116 in memory 58. Object detection subsystem 52 then calculates 118 the total mass of the next 2D slice and compares 120 the total mass of the 2D slice to the threshold value as described above.

Object detection subsystem 52 notifies reconstruction subsystem 56 that trailing edge 64 of object 24 has been detected 124. In one embodiment, object detection subsystem 52 notifies reconstruction subsystem 56 via one or more transmitted signals. Alternatively, object detection subsystem 52 notifies reconstruction subsystem 56 in any suitable manner that enables control system 26 to operate as described herein. Reconstruction subsystem 56 aggregates 126 the 2D slices sequentially between leading edge 62 and trailing edge 64 of object 24. Reconstruction subsystem 56 reconstructs 128 the aggregated 2D slices into a three-dimensional (3D) image of object 24. More specifically, reconstruction subsystem 56 executes at least one reconstruction algorithm on the aggregated 2D slices. One such reconstruction algorithm that may be used is a Ray Consistency Based Reconstruction algorithm described in U.S. Patent Application Publication Number 2008/0192886. Alternatively, any reconstruction algorithm may be used that enables reconstruction subsystem 56 to operate as described herein. After reconstructing 128 a 3D image of object 24, reconstruction subsystem 56 stores 130 the 3D image in memory 58 and optionally displays 132 the 3D image to a user via display device 30 (shown in FIG. 1).

In the exemplary embodiment, control system 26 reduces a power usage of scanning system 10 if no objects 24 are detected within a time period. More specifically, in the exemplary embodiment, acquisition subsystem 54 monitors 140 the detection 114 of a leading edge 62 of an object 24 by object detection subsystem 52 while acquisition subsystem 54 continuously scans 102 CT plane 38. In the exemplary embodiment, a timer (not shown) within control system 26 continuously counts down from a predetermined time to zero. In the exemplary embodiment, the predetermined time is approximately 15 minutes, but any suitable amount of time that enables control system 26 to operate as described herein may be used. In the exemplary embodiment, detection 114 of a leading edge 62 of an object 24 resets the timer to the predetermined time, and acquisition subsystem 54 continues to scan 102 CT plane 38 as described above. If acquisition subsystem 54 determines 142 that no leading edge 62 of an object 24 is detected 114 before the timer reaches zero, scanning system 10 (shown in FIG. 1) enters 144 a low power state. In the exemplary embodiment, scanning system 10 enters 144 a low power state by substantially de-energizing a radiation source 32 and/or detector 36. In an alternative embodiment, scanning system 10 enters 144 a low power state by substantially de-energizing any combination of scanning system 10 components. In an alternative embodiment, scanning system 10 enters 144 a low power state by placing one or more components of scanning system 10 into a sleep state, a hibernation state, and/or a suspend state.

After scanning system 10 has entered 144 into a low power state, backup detector 74 (shown in FIG. 2) continuously monitors the entrance to CT plane 38. In the exemplary embodiment, motion detector 70 monitors light sensor 68 to detect 146 when object 24 is approaching or entering CT plane 38. Motion detector 70 notifies control system 26 if object 24 is approaching or entering CT plane 38. Upon such notification, scanning system 10 operates 148 at a full power state and resumes operation as described herein.

In an alternative embodiment, control system 26 may use a first rebinning resolution to determine leading edge 62 of object 24, and a second rebinning resolution to reconstruct 128 a 3D image of object 24 between leading edge 62 and trailing edge 64. More specifically, control system 26 may reduce a resolution and/or a sampling rate used to rebin 106 the raw data into 2D sinograms until leading edge 62 of object 24 is detected 114. Once leading edge 62 is detected 114, control system 26 may increase the resolution and/or the sampling rate used to rebin 106 the raw data into 2D sinograms until trailing edge 64 of object 24 is detected 124. As such, control system 26 may facilitate a fast, low resolution determination of leading edge 62 of object 24 and a high resolution reconstruction 128 of an interior of object 24 between leading edge 62 and trailing edge 64.

In the exemplary embodiment, steps of method 100 are described above as being performed by individual subsystems of control system 26. In alternative embodiments, each step of method 100 may be performed by any of object detection subsystem 52, acquisition subsystem 54, and/or reconstruction subsystem 56. Moreover, each of object detection subsystem 52, acquisition subsystem 54, and reconstruction subsystem 56 may perform one or more steps of method 100 in parallel.

The above-described embodiments facilitate continuously scanning a stream of objects. More specifically, the embodiments described herein enable a scanning system to more accurately determine a leading edge and a trailing edge of an object. An amount of processing is reduced by eliminating image reconstruction during times when an object is not present within the scanning system. More specifically, the embodiments described herein perform three-dimensional image reconstruction only of object data between a leading edge and a trailing edge of an object. Moreover, reconstructing only the actual object data enables the scanner to keep pace with the conveyor without requiring frequent stops and starts of the conveyor. Furthermore, determining the leading edge and the trailing edge of objects by calculating a total mass in rebinned two-dimensional slices facilitates reducing a number of image detection errors generated by the scanner. In addition, tracking the leading edge and the trailing edge of each object enables each object to be tracked through the acquisition processing, which enables a correspondence to be established and/or communicated between the scanning system and an external device, such as a baggage handling system.

A technical effect of the systems and method described herein includes at least one of: (a) continuously acquiring raw data of a stream of objects using an X-ray system, (b) rebinning raw data of a stream of objects into at least one two-dimensional sonogram, (c) determining a leading edge and a trailing edge of a first object of a stream of objects from at least one two-dimensional sonogram, and (d) reconstructing a three-dimensional image of a first object of a stream of objects using at least one two-dimensional sinogram.

Exemplary embodiments of systems and methods for performing a scan of an object are described above in detail. The systems and method are not limited to the specific embodiments described herein, but rather, components of the systems and/or steps of the method may be utilized independently and separately from other components and/or steps described herein. For example, the method may also be used in combination with other scanning systems and methods, and is not limited to practice with the computed tomography systems as described herein. Rather, the exemplary embodiment may be implemented and utilized in connection with many other imaging applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for scanning a stream of objects, said method comprising:
    continuously acquiring raw data of the stream of objects using an X-ray system, the X-ray system including a detector;
    rebinning the raw data of the stream of objects into at least one two- dimensional sinogram using a first resolution;
    determining a leading edge and a trailing edge of a first object of the stream of objects from the at least one two-dimensional sinogram, wherein the raw data is rebinned using a second resolution different from the first resolution after the leading edge is detected; and
    reconstructing a three-dimensional image of the first object using the at least one two-dimensional sinogram.

2. A method in accordance with claim 1, further comprising placing the X-ray system in a low power state if no leading edge is determined within a period of time.

3. A method in accordance with claim 2, further comprising restoring the X-ray system to a full power state after detecting a second object of the stream of objects.

4. A method in accordance with claim 3, further comprising using a light sensor to detect the second object.

5. A method in accordance with claim 1, wherein said determining a leading edge comprises:
    calculating a mass represented by the at least one two-dimensional sinogram;
    comparing the mass to a threshold; and
    identifying the leading edge if the mass of the at least one two- dimensional sinogram is greater than the threshold.

6. A method in accordance with claim 1, wherein said determining a trailing edge comprises:
    calculating a mass represented by the at least one two-dimensional sinogram;
    comparing the mass to a threshold; and
    identifying the trailing edge if the mass of the at least one two- dimensional sinogram is less than the threshold.

7. A method in accordance with claim 1, wherein the X-ray system includes a memory, said reconstructing a three-dimensional image comprises storing in the memory each two-dimensional sinogram of the at least one two-dimensional sinogram between the leading edge and the trailing edge.

8. A method in accordance with claim 7, wherein said reconstructing a three-dimensional image further comprises:
    aggregating each two-dimensional sinogram between the leading edge and the trailing edge; and
    executing a reconstruction algorithm on the aggregation of two-dimensional sinograms.

9. A method in accordance with claim 8, further comprises discarding the at least one two-dimensional sinogram if the at least one two-dimensional sinogram is not between the leading edge and the trailing edge.

10. A scanning system, comprising:
    a conveyor configured to transport a stream of objects through said scanning system; and
    a computed tomography (CT) system configured to generate an image of a first object of the stream of objects, said CT system comprising a detector and a control system, said control system configured to:
        continuously acquire raw data of the stream of objects from said detector;
        rebin the raw data of the stream of objects into at least one two- dimensional sinogram using a first resolution;
        determine a leading edge and a trailing edge of the first object from the at least one two-dimensional sinogram, wherein the raw data is rebinned using a second resolution different from the first resolution after the leading edge is detected; and
        reconstruct a three-dimensional image of the first object using the at least one two-dimensional sinogram.

11. A scanning system in accordance with claim 10, wherein said control system is further configured to:
    calculate a mass represented by the at least one two-dimensional sinogram;
    compare the mass to a threshold; and
    identify the leading edge if the mass of the at least one two-dimensional sinogram is greater than the threshold.

12. A scanning system in accordance with claim 10, wherein said control system is further configured to:
    calculate a mass represented by the at least one two-dimensional sinogram;
    compare the mass to a threshold; and
    identify the trailing edge if the mass of the at least one two-dimensional sinogram is less than the threshold.

13. A scanning system in accordance with claim 10, wherein said scanning system enters a low power state if no leading edge is determined within a period of time.

14. A scanning system in accordance with claim 13, wherein said scanning system is restored to a full power state after detecting a second object of the stream of objects.

15. A scanning system in accordance with claim 14, wherein said scanning system uses a light sensor to detect the second object.

16. A scanning system in accordance with claim 10, wherein said CT system comprises a memory, said CT system further configured to store in said memory each two-dimensional sinogram of the at least one two-dimensional sinogram between the leading edge and the trailing edge.

17. A scanning system in accordance with claim 16, wherein said CT system is further configured to:
    aggregate each two-dimensional sinogram between the leading edge and the trailing edge; and
    execute a reconstruction algorithm on the aggregation of two-dimensional sinograms.

18. A computed tomography (CT) system, comprising:
    a radiation source;
    a detector configured to detect radiation emitted from said radiation source; and
    a control system comprising:
        an acquisition subsystem configured to continuously acquire raw data of a stream of objects from said detector;
        an object detection subsystem configured to:
            rebin the raw data of the stream of objects into at least one two- dimensional sinogram using a first resolution; and
            determine a leading edge and a trailing edge of a first object of the stream of objects from the at least one two-dimensional sinogram, wherein the raw data is rebinned using a second resolution different from the first resolution after the leading edge is detected; and a reconstruction subsystem configured to reconstruct an image of the first object using the at least one two-dimensional sinogram.

19. A CT system in accordance with claim 18, wherein said control system is further configured to:

calculate a mass represented by the at least one two-dimensional sinogram;

compare the mass to a threshold; and identify the trailing edge if the mass of the at least one two-dimensional dimensional sinogram is less than the threshold.

20. A CT system in accordance with claim 18, further comprising a gantry rotatable about a CT plane within said CT system, said radiation source and said detector coupled to said gantry for rotation about said CT plane.

* * * * *